United States Patent [19]
Blevins

[11] Patent Number: 4,601,717
[45] Date of Patent: Jul. 22, 1986

[54] DIAPER WITH FOLD POINTS

[75] Inventor: John M. Blevins, Bonn, Fed. Rep. of Germany

[73] Assignee: The Procter & Gamble Company, Cincinnati, Ohio

[21] Appl. No.: 678,620

[22] Filed: Dec. 6, 1984

[30] Foreign Application Priority Data

Dec. 8, 1983 [GB] United Kingdom ............... 8332828

[51] Int. Cl.$^4$ ........................................... A61F 13/16
[52] U.S. Cl. ............................................. 604/358 A
[58] Field of Search ............... 604/385 R, 385 A, 366, 604/358, 359

[56] References Cited

U.S. PATENT DOCUMENTS

| | | | |
|---|---|---|---|
| 3,884,234 | 5/1975 | Taylor | 604/385 R |
| 3,926,189 | 12/1975 | Taylor | 604/359 |
| 3,938,523 | 2/1976 | Gilliland et al. | 604/385 R |
| 4,300,562 | 11/1981 | Pieniak | 604/385 A |

FOREIGN PATENT DOCUMENTS 2023431 1/1980 United Kingdom ............ 604/385 R

Primary Examiner—John D. Yasko
Attorney, Agent, or Firm—John M. Pollaro; Fredrick H. Braun; Richard C. Witte

[57] ABSTRACT

A disposable diaper, or similar article, with elastic sidebands, is folded to bring the elastics into a curvilinear shape, thereby improving fit around the legs.

7 Claims, 4 Drawing Figures

DIAPER WITH FOLD POINTS

TECHNICAL FIELD

The present invention relates to absorbent structures, especially disposable baby diapers, adult incontinence products, and the like.

BACKGROUND

A goal in the manufacture of diapers is to find a structure which is sufficiently inexpensive to manufacture and sell that it can be disposed of after a single use, yet has waste containment equivalent to cloth diapers, or cloth diapers with plastic overpants. One major problem in developing such a structure is to provide an appropriate, non-leaking fit around the leg openings. This search for an improved disposable diaper structure has been going on for the past two decades.

One method to achieve good leg fit in a rectangular disposable diaper is to use the so-called Z-fold configuration as described in U.S. Pat. No. RE 26,151.

Another method to achieve even better fit is to use elastic bands running length-wise along the sides of the diaper to provide elasticized leg openings, in-use and/or to shape the diaper into a non-rectangular (generally, "hourglass") shape that, in-use, conforms rather well to the legs. See U.S. Pat. No. 3,860,003.

In approaching this problem of leg openings, it may be speculated that it would be possible to improve leg fitment even further if the elastic bands could simply be provided in a curvlinear configuration. In-use, the curvilinear elastic would be fitted around the legs, substantially in the manner of circularly-elasticized non-disposable undergarments. Of course, this would require that the elastics be affixed to the diaper in a curvilinear configuration, rather than in the "in-line" elasticization mode used in all current elasticized disposable diapers. See U.S. Pat. No. 4,081,301 for a description of a preferred method for in-line elasticizaton of disposable diapers.

However, on further consideration it is clear that applying elastics in other than a substantially in-line configuration would be quite expensive and not conducive to the efficient, high-speed manufacture of disposable diapers.

The present invention provides a preferred structure for a disposable diaper, or the like, whereby elastics applied substantially in-line with the absorbent core are made to assume a curvilinear shape. This is achieved by constructing the diaper and folding it, in the manner described hereinafter. The resulting structure exhibits improved leg fitment, better waste containment, and is more comfortable than either folded (but non-elasticized) or in-line elasticized (but non-folded) diapers of the prior art.

SUMMARY OF THE INVENTION

The present invention encompasses absorbent structures such as disposable diapers, or the like. As is well-known in the art, such diapers will comprise: a backsheet (the sheet used outermost from the skin, and which is generally made from urine-impenetrable plastic material to give the containment effect of plastic pants); a core that will absorb and help contain urine and/or fecal matter; and, generally, a topsheet (the sheet closest to the skin) that is urine-permeable.

Elasticized diapers have, in addition to the above elements, one or more elastic bands running substantially along each side. In use, such bands are fitted around the legs to provide elasticized leg-openings. In the preferred diaper structure described in U.S. Pat. No. 3,860,003, the backsheet is somewhat broader than the core, and the elastics are positioned outwardly from the core to provide a spacing element, or flexible side-flat, that substantially enhances performance.

In the present invention, the basic diaper structure is generally similar to that disclosed in U.S. Pat. No. 3,860,003, but is further characterized by one or more fold points on one, or most preferably both, sides of the diaper, whereby the spacing elements are folded over and affixed at one (preferred) or more points to the topsheet or to the absorbent core. Thus, the elastics, which have been applied in a substantially in-line configuration, are thereby forced into a curvilinear shape.

Figure 1:
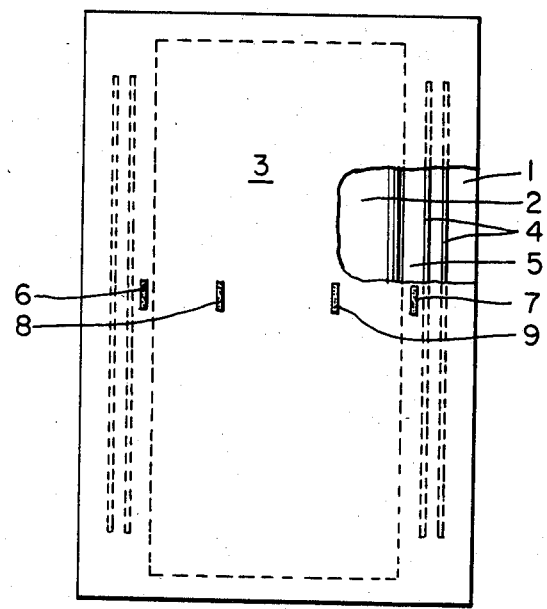
FIG. 1 depicts a plan view of an flattened rectangular diaper of the present type prior to folding, showing backsheet (1), core (2), topsheet (3) and elastics (4). The elastics shown in FIG. 1 are positioned outwardly from the side edges of core (2) to provide spacing element (5) along each side of the core. Points (6) and (7) are fold-points which, in the final diaper, are affixed to contact points (8) and (9), respectively, of the core/topsheet assembly, hereby forcing the elastics to curve. The degree of curvature can be varied by varying the width of the spacing element, moving the contact points, etc.
Figure 2:
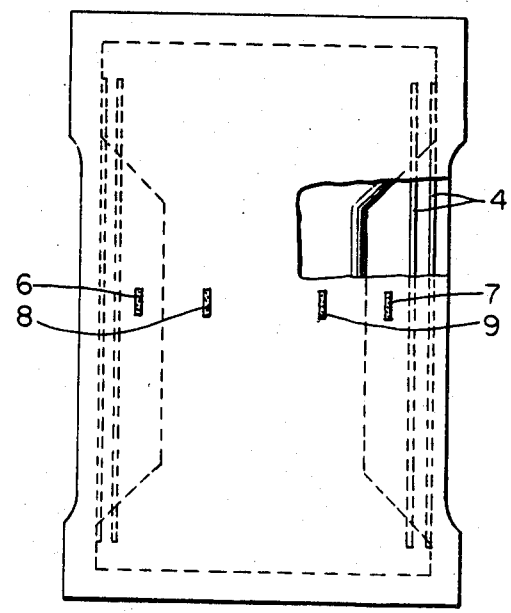
FIG. 2 shows a more preferred diaper of the present type, again in flattened plan view, wherein the core, the backsheet, and preferably, the topsheet, are all in a preferred shape ("hourglass") configuration. Again, fold-points (6) and (7) are affixed to contact points (8) and (9) in the final diaper.

It is to be understood that multiple fold-points may be employed in the diapers, and that the drawings are provided only as a means of better illustrating the structures of this invention. The cores may be rectangular, T-shaped, I-shaped, wedge-shaped, hourglass-shaped (preferred), and the like, according to the desires of the manufacturer.

It is also to be understood that the terms "fold-points" and "contact-points" may be either a point described as by a drop of adhesive, or may be a line of adhesive or other fastening means. Obviously, a line of adhesive (say 2.5 cm) will give a stronger bond at the place of contact than will a drop of the same adhesive. This can be decided by the manufacturer.

DETAILED DESCRIPTION

The articles disclosed herein can be prepared using materials that are very well known in current commercial practice, and reference can be made to the various patents mentioned hereinbefore and to the general disposable diaper patent literature and trade catalogues for such materials. Likewise, methods and apparatus for assembling disposable diapers are known from patents and engineering literature.

While materials used in the assembly of disposable diapers and the like are well-known, the following may be mentioned solely by way of example. It is to be understood that the present invention resides in the assembly of such materials, or their equivalents, into the folded absorbent structures disclosed herein, rather than in the materials per se.

Backsheet: The backsheet can comprise a urine-impervious polymer sheet, for example polyethylene or polypropylene, that is thin enough to be flexible. A polyethylene sheet 0.01–2 mm thick is typical.

Absorbent Core: The core can comprise any urine-absorbent material, such as cotton cloth, cellulose fibres, "super-absorbent" polymers such as the polyacrylamides, and the like. Air-laid felt comprising compacted cellulosic fibres is typical, especially when formed as a flexible mat having a Taber stiffness of about 7, and above.

Topsheet: The topsheet can comprise any loosely-woven or nonwoven cloth or scrim-type material that is urine-porous and comfortable to the skin. A nonwoven sheet comprising polypropylene fibres is typical.

Elastic Members: The elastics can comprise elastic bands or threads, or elastic adhesive applied as a band or ribbon. One or more elastics can be applied longitudinally along both sides of the diaper, and laid-down either on the topsheet, on the backsheet, or sandwiched between said sheets. In a typical mode, the elastic is pre-stretched, then glued to the diaper using an elastic adhesive, all in well-known fashion. (See U.S. Pat. No. 4,081,301.)

Fasteners: The absorbent structures can be fastened by any convenient means, such as pins, snaps and the like. Typical fasteners comprise adhesive tapes, especially tapes in the "Y" configuration described in the patent literature.

Assembly Means: The articles herein can be assembled by any convenient bonding means, such as heat-sealing, ultrasonic sealing, and the like. Typically, urine-stable adhesives are used to assembly disposable diapers.

Assembly Methods and Apparatus: The apparatus used to form the absorbent articles herein constitutes no part of the present invention. Indeed, such articles may be assembled by hand. However, briefly considering the sophisticated technology embodied in the high-speed, automatic assembly of disposable diapers by art-disclosed machinery may assist in the appreciation of the practicality of the present invention.

A tyical diaper assembly system comprises means to: (1) lay-down the backsheet; (2) position the core on the backsheet; (3) position the topsheet over the core; (4) stretch and glue-down the elastics; (5) fasten the topsheet to the backsheet; and (6) affix fastener tapes, all more-or-less in that sequence. All sheet material and the elastics are generally introduced onto a unidirectional moving belt as continuous items, which are assembled, then cut into individual diapers at the end of the line. All operations are done "in-line", at the rate of hundreds of diapers per minute. Thus, it will be appreciated that any operation that cannot be accomplished in-line (for example, somehow turning the in-line flow of diapers to allow elastics to be applied curvilinearly) slows production dramatically.

In the present invention the diapers can be manufactured and folded in-line by, for example, allowing the leading edges of the diaper to enter a folding device, or "flap" arrangement, which laps the spacing elements over and brings fold points (6 and 7) into contact with, for example, glue beads or glue lines affixed at any pre-selected contact points (8 and 9 in the Figures), thereby achieving a fold on each side of the diaper which bends the elastics into a curvilinear configuration. (The construction of a folding device can follow the general structural features of an automatic envelope flap sealer of the type well-known in commercial postage meters, and the like.) Other means of achieving the folds using robotics, or manual folding, will be apparent to one skilled in the art.

INDUSTRIAL APPLICATION

The following Example illustrates a preferred diaper made according to the present invention. The dimensions listed in the Example are for a diaper intended for use with a child in the 6 to 10 kilogram size range. These dimensions can be modified proportionately for different size children, or for adult incontinence briefs, according to standard commercial practice.

EXAMPLE I

Figure 3:
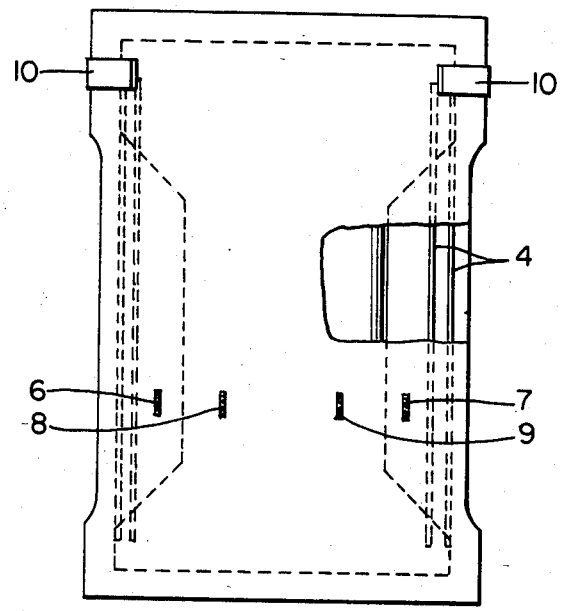
FIG. 3 depicts a flattened plan view of a most preferred embodiment of the present invention, which optionally also has tape fasteners (10) affixed to both sides of the diaper. Fold-points (6) and (7) and contact points (8) and (9) are displaced forward of the longitudinal midpoint in the FIG. 3 diaper. The diaper is folded to juxtapose points (6) with (8) and (7) with (9), the resulting folds being held, for example, by glue spots. In-use, the diaper is placed around the child with the tapes to the rear, and with the fold described by the juxtaposition of the fold points with the contact points being towards the front of the child. The tape fasteners are then used to hold the diaper in place, in the manner described in U.K. Pat. No. 1,458,566, which describes a preferred "Y-tape" diaper fastener. Displacing the fold provides an especially comfortable diaper, and tends to hold the absorbent core slightly away from the child's genital and peri-anal areas, thereby desirably decreasing contact between bodily waste products on the absorbent pad with the child's skin.
Figure 4:
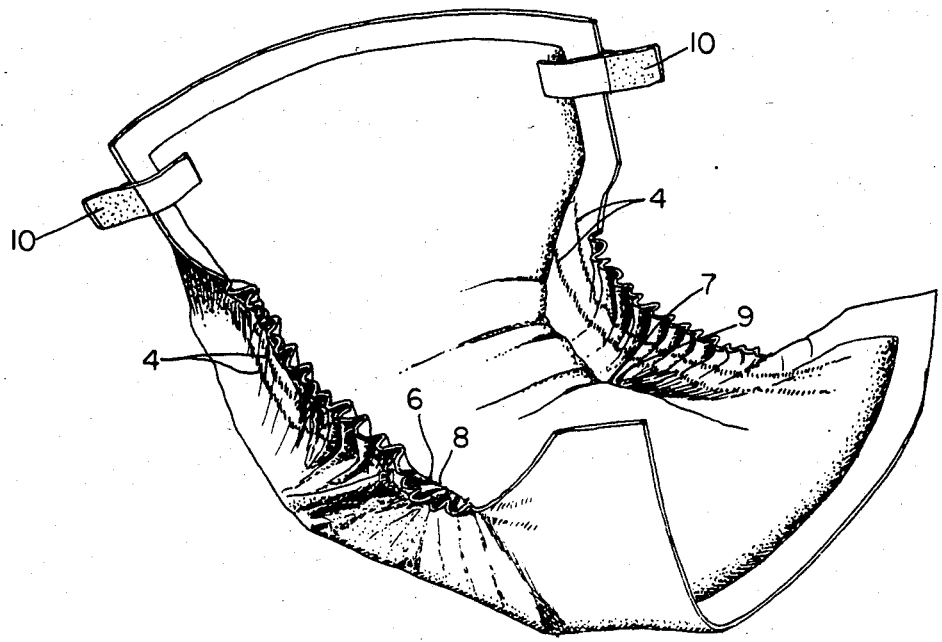
FIG. 4 shows the article of FIG. 3 fully-assembled and illustrates the curvilinear shape of the elastics caused by the folding.

A diaper according to FIG. 3 is assembled the following materials and folded to the FIG. 4 configuration.

1. Backsheet: 0.025–0.070 mm polyethylene: width at top and bottom 33 cm; notched inwardly on both sides to a width-at-center of 28.5 cm; length 50.2 cm.

2. Topsheet: spun-bonded polypropylene, basis weight 21.5 g/m$^2$–24.5 g/m$^2$; width at top and bottom 33 cm; notched inwardly on both sides to a width-at-center of 28.5 cm; length 50.2 cm.

3. Absorbent core: air-laid wood pulp fibers, Taber range 7–9.5, 8.4 mm thick, calendared; width at top and bottom 28.6 cm; notched inwardly at both sides to a width-at-center of 10.2 cm; length 44.5 cm.

4. Elastics: four individual rubber strips (2 per side); width 4.77 mm; length 370 mm; thickness 0.178 mm (all the foregoing dimensions being in the relaxed state.)

The diaper of Example I is prepared in standard fashion by positioning the core covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2-bands per side) of the core. The inner bands along each side are positioned ca. 55 mm from the narrowest width of the core (measured from the inner edge of the elastic band). Stated otherwise, the inner band and the edge of the shaped core approximate an arc of a circle having a radius of 528 RAD. This provides a spacing element along each side of the diaper comprising the flexible topsheet/backsheet material between the inner elastic and the curved edge of the core. The inner bands are glued down along their length in the stretched state. The outer bands are positioned ca 13 mm from the inner bands, and are glued down along their length in the stretched state. Since the topsheet/backsheet assembly is flexible, the glued-down bands contract to elasticize the sides of the diaper.

The elasticized diaper prepared in the foregoing manner is flattened preparatory to folding in the manner of this invention. Contact points 8 and 9 are selected on the topsheet. In this preferred embodiment, the contact points 8 and 9 are displaced towards what will be the front of the diaper, in-use, as shown in FIGS. 3 and 4. For this size diaper, the contact points are positioned on the topsheet over the core about 16.5 cm from the end edge of the core and about 30 mm inward from the left and right edges of the core, respectively. Glue beads or glue lines are placed at each contact point.

Fold points 6 and 7 are selected on each spacing element. In this preferred embodiment, the fold points are each selected on their respective spacing elements approximately 30 mm from the edge of the diaper core and are each displaced away from the longitudinal mid-point of the diaper towards the front of the diaper (i.e., downward in FIG. 3) to a point about 16.5 cm measured from the end of the core.

Fold points 6 and 7 are brought over in a simple fold into contact with the glue at contact points 8 and 9, respectively, and sealed. This results in the structure depicted in FIG. 4. Fastener tapes are optionally, and preferably, affixed to the diaper as shown in the Figures.

In-use, the diaper of Example I is positioned on the child with the fastener tapes at the back and the folds at the front of the child. The elastics on both sides of the diaper are in the form of upward and outward-facing, curvilinear leg openings which snugly conform themselves around the child's legs when the fastener tapes are attached to the front of the diaper to hold it in place.

It will be appreciated by those skilled in the art that the folds herein can be on either, or most preferably both, sides of the diaper. While Example I employs a preferred non-rectangular shaped core/backsheet/topsheet assembly, rectangular diapers may also be assembled and folded in the manner disclosed herein. In an alternate mode, the core may be non-rectangular, and the backsheet rectangular, and vice-versa.

It will be further appreciated that the present invention encompasses not only the diaper structures, but also the method for converting essentially linearly-applied elastic members in an absorbent diaper, or the like, into curvilinear elastic members by folding in the manner disclosed herein. Of course, the degree of curving of the elastics can be routinely adjusted according to the desires of the manufacturer by adjusting such parameters as the width of the spacing element, positioning of the contact points, shaping of the core/backsheet/topsheet, and the like.

Importantly, by selecting a fold position away from the longitudinal mid-point of the diaper (e.g., 2–5 cm forward in a 6–10 Kg diaper) a bulge or "pocket" is created in the diaper which tends to hold it away from the skin, in-use.

Moreover, the folds used in the present diapers are made using the spacing element, and the core, itself, is not folded over, since folding the core would lead to bunching and discomfort to the user.

I claim:

1. An absorbent structure, comprising a backsheet, absorbent core, a topsheet, and at least one elastic member along each longitudinal side of the structure, said elastic member being situated away from said absorbent core to provide flexible spacing elements; said spacing elements being folded over said absorbent core at at least one fold point and being affixed to said topsheet at at least one contact point, whereby at least one said elastic member is bent from its original configuration into a curvilinear shape, thereby providing an improved leg opening for the absorbent structure.

2. A structure according to claim 1 wherein said spacing elements are folded over and affixed at at least one contact point, thereby providing generally outward-facing, curvilinearly-elasticized leg openings.

3. A structure according to claim 2 wherein said absorbent core and said backsheet, are substantially rectangular.

4. A structure according to claim 2 wherein said absorbent core, is substantially non-rectangular.

5. A structure according to claim 4 wherein said absorbent core, said backsheet and said topsheet have an hourglass configuration.

6. A structure according to claims 1, 2, 3, 4, or 5 wherein said fold point and corresponding said contact point are displaced away from the longitudinal midpoint of the absorbent structure.

7. A structure according to claim 6 wherein said fold point and said contact point are displaced towards the front of the absorbent structure.

* * * * *

UNITED STATES PATENT AND TRADEMARK OFFICE
CERTIFICATE OF CORRECTION

PATENT NO. : 4,601,717

DATED : 7/22/86

INVENTOR(S) : John M. Blevins, et. al.

It is certified that error appears in the above-identified patent and that said Letters Patent is hereby corrected as shown below:

Column 2, at line 6: delete "side-flat" and insert --side-flap--

Column 4, at line 47: delete "fibers" and insert --fibres--

Signed and Sealed this

Seventh Day of October, 1986

[SEAL]

Attest:

DONALD J. QUIGG

Attesting Officer

Commissioner of Patents and Trademarks